(12) United States Patent
Boyd et al.

(10) Patent No.: US 7,972,368 B2
(45) Date of Patent: Jul. 5, 2011

(54) REFILLABLE THERAPEUTIC PACK

(75) Inventors: Michael S. Boyd, Asheville, NC (US); Robert S. Woody, Brevard, NC (US)

(73) Assignee: Precept Medical Products, Inc., Arden, NC (US)

( * ) Notice: Subject to any disclaimer, the term of this patent is extended or adjusted under 35 U.S.C. 154(b) by 0 days.

(21) Appl. No.: 11/094,046

(22) Filed: Mar. 30, 2005

(65) Prior Publication Data

US 2005/0222655 A1 Oct. 6, 2005

Related U.S. Application Data

(60) Provisional application No. 60/558,430, filed on Apr. 1, 2004.

(51) Int. Cl.
*A61F 7/10* (2006.01)
(52) U.S. Cl. ........................ 607/114; 607/108
(58) Field of Classification Search .......... 607/108–112, 607/114
See application file for complete search history.

(56) References Cited

U.S. PATENT DOCUMENTS

| | | | |
|---|---|---|---|
| 1,403,287 A | 1/1922 | Brisbine | |
| 2,273,128 A * | 2/1942 | Madsen et al. | 383/91 |
| 4,347,848 A | 9/1982 | Hubbard et al. | |
| 4,385,950 A | 5/1983 | Hubbard et al. | |
| 4,408,643 A * | 10/1983 | Laske et al. | 383/70 |
| 4,688,572 A | 8/1987 | Hubbard et al. | |
| 4,951,666 A | 8/1990 | Inman et al. | |
| 5,044,774 A | 9/1991 | Bullard et al. | |
| 5,074,300 A * | 12/1991 | Murphy | 607/108 |
| 5,356,426 A * | 10/1994 | Delk et al. | 607/112 |
| 5,534,020 A | 7/1996 | Cheney, III et al. | |
| 5,641,325 A | 6/1997 | Delk et al. | |
| 5,723,002 A | 3/1998 | Delk et al. | |
| 6,022,144 A | 2/2000 | Hausslein | |
| 6,149,305 A * | 11/2000 | Fier | 383/91 |
| 6,273,608 B1 | 8/2001 | Ward, Jr. et al. | |

* cited by examiner

*Primary Examiner* — Henry M Johnson, III
*Assistant Examiner* — Aaron Roane
(74) *Attorney, Agent, or Firm* — Thorp Reed & Armstrong, LLP

(57) ABSTRACT

A refillable therapeutic pack is disclosed that is comprised of an outer bag having a generally rectangular shape having two sides, a closed end and an open end. Tie straps are secured on the outer bag near the closed end and the open end and extend from the ends. An inner bag is provided internally within the outer bag. The inner bag has two sides, a closed end attached to the closed end of the outer bag and an open end. The open end of the inner bag is of a smaller diameter than the closed end of the inner bag such that the open end of the inner bag contains a neck section. Ice or cooling material may be filled into the inner bag of the cold pack through the neck section of the open end of the inner bag. The cold pack additionally includes flexible opening aids contained within the neck section of the open end to aid in opening and holding open the open end of the inner bag during filling and emptying. The cold pack additionally includes attachment wings to attach the side of the inner bag to the side of the outer bag to hold the inner bag in place. Further, the cold pack includes a sleeve for holding a clip or closure device when the clip or closure device is not in use. The clip or closure device is used to seal and close the inner bag after the inner bag is filled with cooling material.

15 Claims, 4 Drawing Sheets

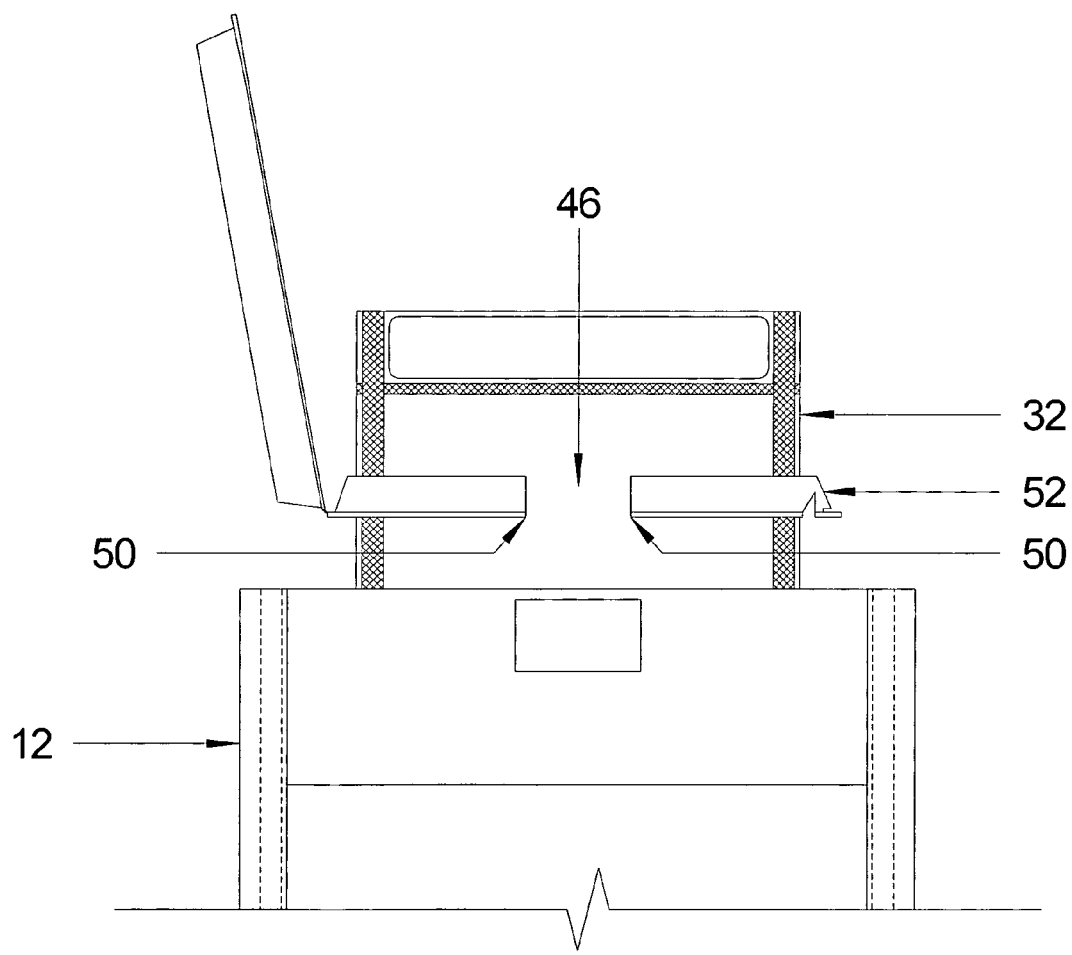

REFILLABLE THERAPEUTIC PACK

The present application claims priority from U.S. Application Ser. No. 60/558,430 filed Apr. 1, 2004 and entitled Refillable Therapeutic Pack, which is hereby incorporated by reference in its entirety.

BACKGROUND OF THE INVENTION

1. Field of the Invention

The present invention relates generally to therapeutic packs and more particularly to refillable cold packs designed for single patient use.

2. Description of the Background

Cold packs or ice packs are oftentimes used for treating specific injuries by cooling or chilling a region of a persons' body. There are a variety of cold packs available for treating specific injuries. One type of cold pack used is a refillable cold pack designed specifically for single patient use.

Cold packs designed for single patient use are oftentimes of a smaller size and difficult to fill. Currently, to fill these types of cold packs the inner bag portion of the cold pack must be manually held open as ice or other cooling material is loaded into the inner bag. Filling in this manner is difficult and oftentimes results in waste and mess. Additionally, filling in this manner is inefficient. Therefore, there is a need in the art for a refillable cold pack designed for single patient use that is easier to fill resulting in less waste, mess and improved efficiency.

Additionally, cold packs designed for single patient use are oftentimes comprised of an inner bag to hold the cold material, such as ice, and an outer bag in which the inner bag is located. One problem that occurs with this design is that once the inner bag is filled with the cold material, it may move around within the outer bag and not hold it's shape relative to the outer bag. This prevents equal distribution of the cold material within the cold pack. Therefore, there is a need for a refillable cold pack designed for single patient use that provides equal distribution of the cold material within the cold pack.

Finally, a clip must be used with the cold packs designed for single patient use to seal and close the inner bag once it is filled with the cooling material. Oftentimes, the clip is attached to the bag with tape. Pieces of tape are commonly used to attach the clip to the bag. However, the tape oftentimes comes loose or tears resulting in the loss of the clip. Additionally, the tape may lose it's ability to hold the clip in place over time. Once the tape comes loose, tears or loses it's ability to hold the clip in place, it becomes difficult and inconvenient to keep the clip and the bag together. Therefore, there is a need in the art for an improved method of holding the bag clip in place on the cold pack when the cold pack is not in use. Additionally, should the clip become separated from the cold pack, there is a need in the art for a method of easily reattaching the clip to the cold pack.

SUMMARY OF THE PRESENT INVENTION

One aspect of the present invention is a cold pack comprising an inner bag attached to an outer bag, opening aids designed to assist in holding open the inner bag, attachment wings for attaching the sides of the inner bag to the sides of the outer bag and a clip sleeve for holding a clip or closing device. The cold pack may additionally comprise tie straps for securing the cold pack onto the portion of the body to be cooled.

BRIEF DESCRIPTION OF THE DRAWINGS

To enable the present invention to be easily understood and readily practiced, the present invention will now be described for purposes of illustration and not limitation, in connection with the following figures wherein:

FIG. 4 illustrates a more detailed view of the clip sleeve of the present invention.

DETAILED DESCRIPTION OF THE INVENTION

Figure 1:
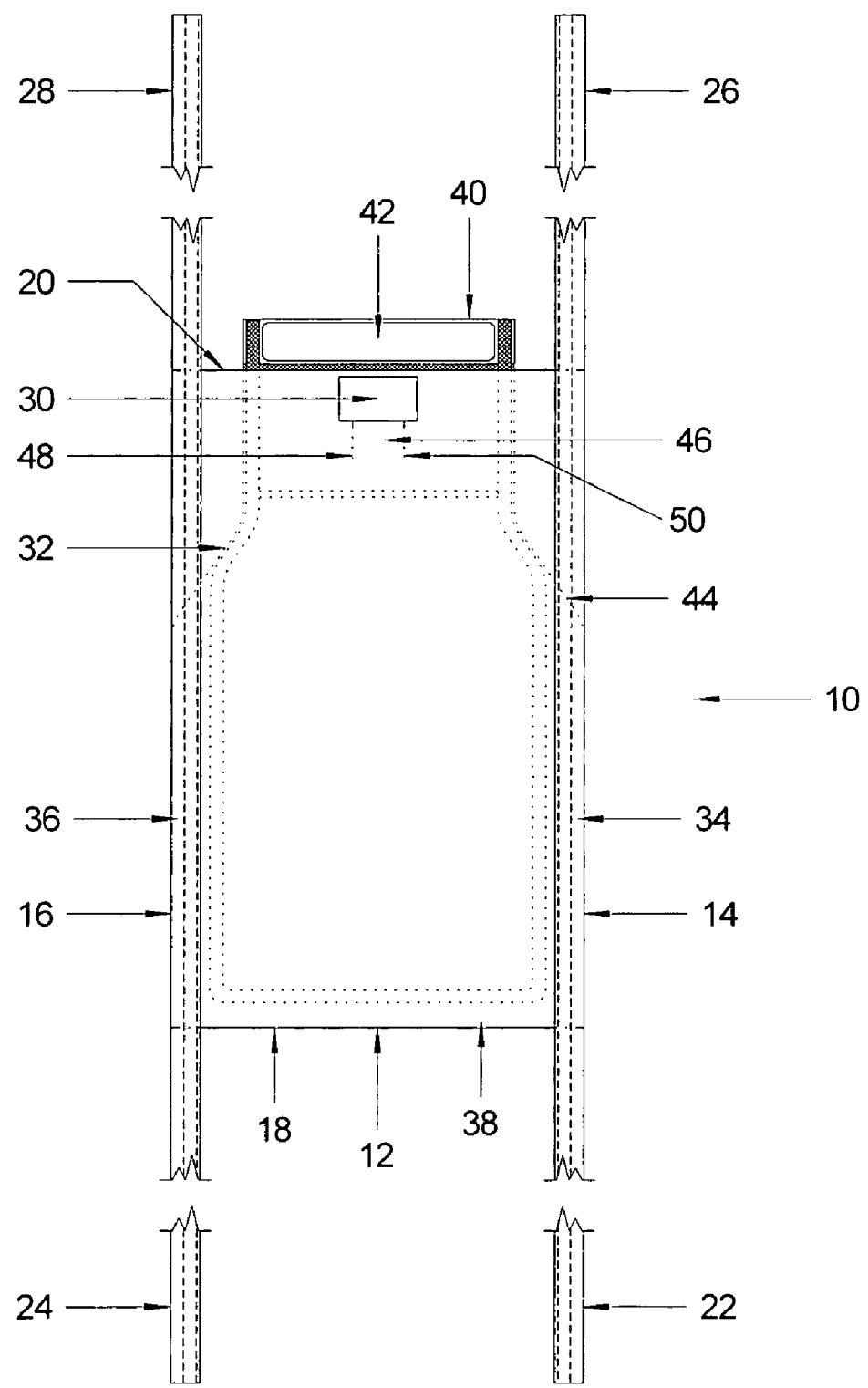
FIG. 1 illustrates a detailed view of the cold pack in accordance with one embodiment.

FIG. 1 shows the cold pack in accordance with one embodiment of the present invention. Cold pack 10 includes a generally rectangularly shaped outer bag 12 having sides 14 and 16, a closed end 18 and an open end 20. Outer bag 12 contains two pair of tie straps 22, 24 and 26, 28 to secure cold pack 10 in place on a patient during use. One pair of tie straps 22, 24 is located near closed end 18 and a second pair of tie straps 26, 28 is located near open end 20. Each pair of tie straps 22, 24 and 26, 28 extend outwardly from outer bag 12. In one embodiment, tie straps 22, 24 and 26, 28 may be attached to outer bag 12 by double stitch sewing. Attaching tie straps 22, 24 and 26, 28 to outer bag 12 by double stitch sewing provides additional strength to the attachment. Alternatively, tie straps 22, 24 and 26, 28 may be attached to outer bag 12 by gluing, heat sealing or ultrasonic welding. Additionally, any other sealing method known in the art may be used. Outer bag 12 may be comprised of a single or multi-layer, woven or non-woven material, and may be comprised of natural and/or synthetic fibers. In one embodiment of the present invention, outer bag 12 is comprised of a combination of short fiber thermo bond polypropylene and rayon/polyethylene spun lace. The thermo bond polypropylene material used in outer bag 12 prevents outer bag 12 from stretching, thus enabling outer bag 12 to retain its shape. Additionally, outer bag 12 may contain a fastener 30 to open and close open end 20 of outer bag 12. Fastener 30 may be any known fastener, such as Velcro, ties, snaps, clips, folding, etc. While specific examples of fastener 30 have been given, those of ordinary skill in the art will recognize that any number of fasteners may be used.

Cold pack 10 additionally includes inner bag 32 designed to hold ice or other cold materials. Inner bag 32 may be a comprised of single or multi-layered plastic or waterproof film. In one embodiment of the present invention, inner bag 32 is comprised of polyethylene film. Inner bag 32 is designed to fit internally within outer bag 12 and is shown in FIG. 1 by broken lines. Inner bag 32 has sides 34 and 36, a closed end 38 and an open end 40. Open end 40 consists of a neck section 41 (see FIG. 2A) that is narrower than closed end 38 of inner bag 32. Ice or other cold materials may be inserted into inner bag 32 through open end 40.

Inner bag 32 is designed to be of sufficient length so that outer bag 12 may be folded back for access to inner bag 32, or the neck section 41 of open end 40 of inner bag 32 may be designed to extend past open end 20 of outer bag 12. This allows for easier filling of cold pack 10. When inner bag 32 of cold pack 10 is filled, the neck section 41 may be folded and sealed with a clip or some other closure device so that outer bag 12 may then be closed around inner bag 32 using fastener 30.

Cold pack 10 additionally contains opening aids/flexible members 42 positioned at open end 40 of inner bag 32.

Figure 2A:
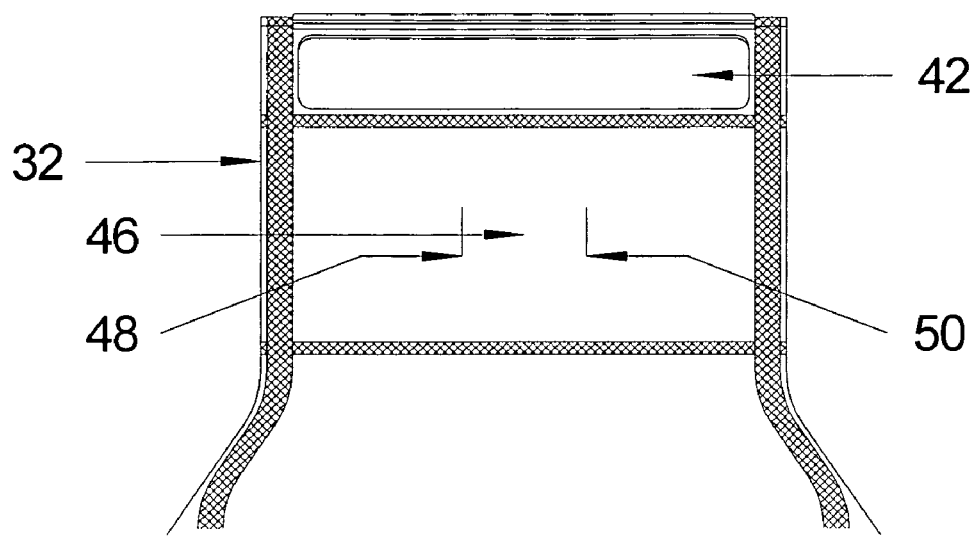
FIGS. 2A and 2B illustrate more detailed views of the opening aids/flexible members of the present invention, located within the inner bag, in unflexed and flexed states, respectively.
Figure 2B:
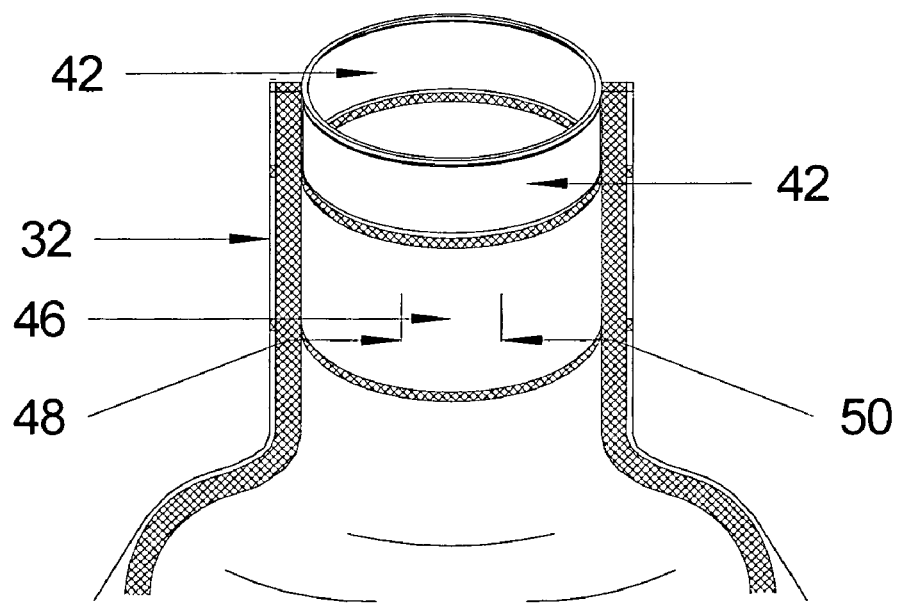

Opening aids 42 may be contained within the top portion of the neck of inner bag 32 one on each side of open end 40. Opening aids 42 in a relaxed state remain flat. FIG. 2A illustrates a more detailed view of opening aids 42 located within inner bag 32 in an unflexed or relaxed state. The application of pressure to the ends of opening aids 42 results in the opposing flexible bars to each form a semi-circular shape producing an oval or circular opening in the top of inner bag 32. FIG. 2B illustrates a more detailed view of opening aids located within inner bag 32 in a flexed state, that is, producing an oval or circular opening in the top of inner bag 32. Opening aids 42 serve to hold open-open end 40 of inner bag 32 to assist the user of cold pack 10 to allow for easier filling or emptying of cold pack 10. Opening aids 42 may consist of flexible bars or members made of plastic or any other type of flexible material that has "memory" such that when a force is applied and movement occurs, the flexible material has the ability to return to its original position once force is removed. Alternatively, the memory may serve to allow the flexible member (opening aid 42) to stay in a flexed position once force is applied and return to its original position upon receiving a force once again.

More specifically, opening aids 42 may have the ability to bend in opposing directions when force is applied, the bending will form generally an ellipse or circle that will aid in the opening of open end 40 of inner bag 32. This bending may also serve to hold open end 40 of inner bag 32 in an "open" position while being filled with ice or other cold materials. Opening aids 42 may be sealed within the structure of open end 40 of inner bag 32. Alternatively, inner bag 32 may have a pocket located at open end 40 of inner bag 32 and opening aids 42 may be inserted within the pocket of open end 40 of inner bag. Further, opening aids 42 may be attached to the inside or outside of inner bag 32 near open end 40. While specific examples have been given, those of ordinary skill in the art will recognize that there are a number of possible placements and manners of arrangement of opening aids 42 to achieve the desired result of assisting in the opening of open end 40 of inner bag 32.

Figure 3:
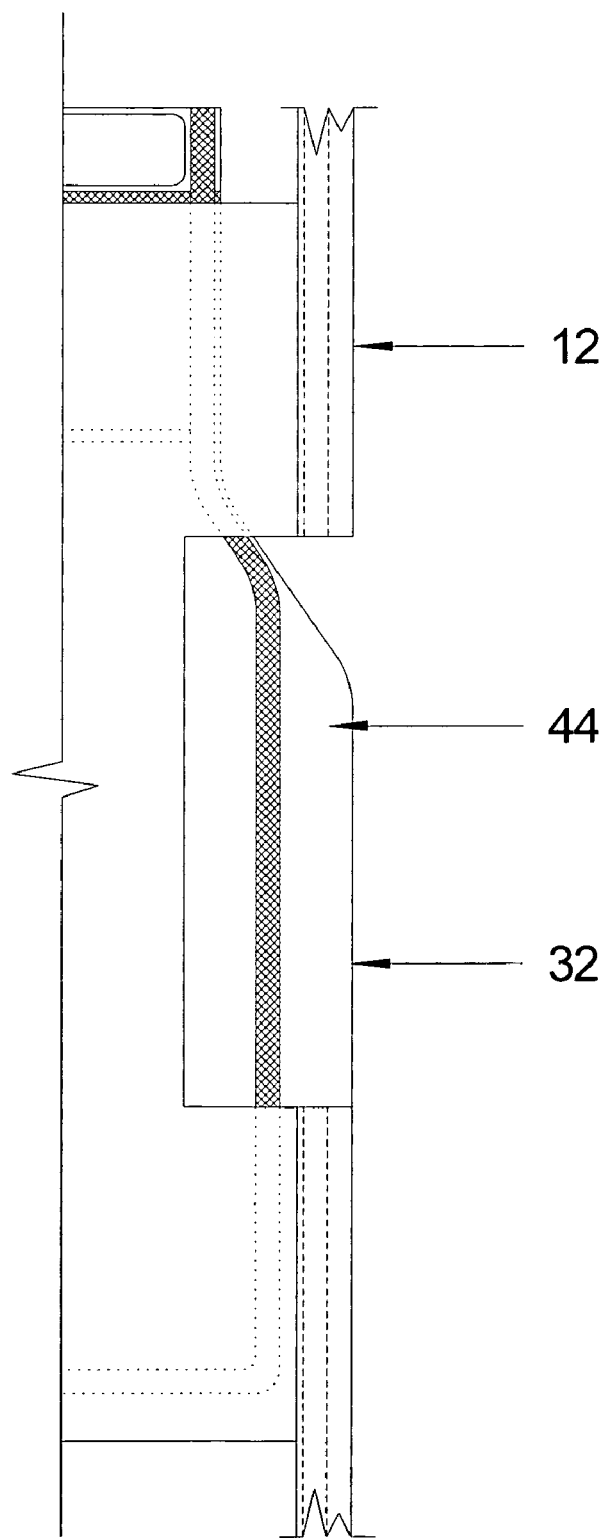
FIG. 3 illustrates a more detailed view of the attachment wings of the present invention.

Additionally, cold pack 10 includes attachment wings 44. FIG. 3. illustrates a more detailed view of attachment wings 44. Attachment wings 44 may be an extension of the sides 34, 36 of inner bag 32 that extend outward beyond the inner perimeter seal of inner bag 32 on both sides 34, 36. Attachment wings 44 may be lengths of film, folded or unfolded, sealed or unsealed, that extend a distance from each sealed side of inner bag 32. Attachment wings 44 may extend along sides 34, 36 of inner bag, from closed end 38 to the neck section 41 of open end 40. Alternatively, attachment wings 44 may be designed to extend a sufficient portion of the length of sides 34, 36 of inner bag, from closed end 38 to the neck section 41 of open end 40. Extensions or attachment wings 44 of inner bag 32 may be sewn into the fabric of outer bag 12 to connect sides 34, 36 of inner bag 32 to sides 14, 16 (respectively) of outer bag 12 up to neck section 41 of inner bag 32. In one embodiment, attachment wings 44 of inner bag 32 may be attached to the fabric of outer bag 12 by double stitch sewing. Attaching attachment wings 44 of inner bag 32 to the fabric of outer bag 12 by double stitch sewing provides additional strength to the attachment. Alternatively, attachment wings 44 may be attached to outer bag 12 by gluing, heat sealing or ultrasonic welding. Additionally, any other sealing method known in the art may be used. Because inner bag 32 is sewn or attached substantially along sides 34, 36 to sides 14, 16 of outer bag 12, inner bag 32 does not move around within outer bag 12 and inner bag 32 holds its shape relative to outer bag 12. Additionally, closed end 38 of inner bag 32 may be sewn or attached to closed end 18 of outer bag 12, to aid in further preventing inner bag 32 from moving around within outer bag 12 and to aid in allowing inner bag 32 to hold its shape relative to outer bag 12. Attachment wings 44 prevent inner bag 32 from sagging within outer bag 12, thus keeping ice distributed more evenly across cold pack 10. This even distribution improves the effectiveness and efficiency of cold pack 10 when used in the treatment of or application to a patient.

As previously mentioned, attachment wings 44 may be sewn into the fabric of outer bag 12 to connect sides 34, 36 of inner bag 32 to sides 14, 16 (respectively) of outer bag 12 up to neck section 41 of inner bag 32. Because inner bag 32 is sewn or attached along sides 34, 66 to sides 14, 16 up to the neck section 41, outer bag 12 may be folded back thus exposing neck section 41 of inner bag 32 to allow for easier filling of inner bag 32. Additionally, after inner bag 32 is filled with ice or substance, neck section 41 of inner bag 32 may be folded in so that inner bag 32 is completely within outer bag 12.

Further, cold pack 10 may include clip sleeve/sleeve 46. FIG. 4 illustrates a more detailed view of clip sleeve 46 of the present invention. As previously mentioned, when inner bag 32 of cold pack 10 is filled, the neck section 41 may be folded and sealed with a clip 52 or some other closure device so that outer bag 12 may then be closed around inner bag 32 using fastener 30. Clip sleeve 46 is designed to hold the clip 52 or closure device that is used to close inner bag 32 in place during transport and use. Clip sleeve 46 is designed to reduce the risk that the clip 52 or closure device will be lost from cold pack 10. Clip sleeve 46 may consist of two opposing slits 48, 50 in a folded portion of inner bag 32, the folded portion of inner bag 32 being sealed at the bottom. The slits may be located in the folded portion of inner bag 32 so that the inside of inner bag 32 is not compromised. A bag clip 52 or closure device may be inserted into one slit and travel within the folded portion of inner bag 32, and will exit out of the opposing slit. The bag clip 52 or closure device may be used as a closure device for sealing the open top portion of inner bag 32.

In another embodiment of the present invention, outer bag 12 is comprised of two layers of non-woven material. In this embodiment, the outer layer of outer bag 12 may be comprised of a medium weight spunlace non-woven material while the inner layer of outer bag 12, that is, the inside layer of outer bag 12 that is adjacent to inner bag 32 may be comprised of a light weight thermal bonded non-woven material, such as a thermal bonded polypropylene. Inside layer of outer bag 12 is preferably comprised of an absorbent material, capable of absorbing moisture. Therefore, the inside layer of outer bag 12 provides strength and durability to cold pack 10, and also reduces or eliminates sweating or condensation that reaches the outer layer of outer bag 12 which layer is in contact with the user.

While the present invention has been described in connection with preferred embodiments thereof, those of ordinary skill in the art will recognize that many modifications and variations are possible. Therefore, it is to be understood that the present invention is not limited to the particular embodiments disclosed, but that it is intended to cover all modifications which are within the true spirit and scope of the invention.

What is claimed is:

1. A cold pack comprising:
   a generally rectangularly shaped outer bag having a closed end, first and second opposing sides and an open end;

an inner bag located, at least in part, within said outer bag, said inner bag having a sealed closed end, a first and second side seals defining opposing sides of said inner bag, and an open end; said open end of said inner bag having a neck section, wherein said neck section is narrower than said sealed closed end of said inner bag;

first and second attachment wings each having an inside boundary and an outside boundary;

wherein each of said side seals has a first side and a second side, said first side of each side seal is directly attached to, or integrally formed with, only said inner bag, and at least a portion of said second side of each side seal is directly attached to, or integrally formed with, said inside boundary of one of said attachment wing;

wherein said first opposing side of said outer bag is directly attached to said first attachment wing at or along a first location other than said inside boundary of said first attachment wing, and said second opposing side of said outer bag is directly attached to said second attachment wing at or along a second location other than said inside boundary of said second attachment wing; wherein said attachments between said outer bag and said first and second attachment wings enable said inner bag to retain its shape relative to said outer bag; and wherein said outer bag is separate from said neck section, in whole or in part, so that said outer bag may be folded or moved away from said neck section to expose said neck section, in whole or in part.

2. The cold pack of claim 1 further comprising:
a first pair of tie straps extending longitudinally from said closed end of said outer bag; and
a second pair of tie straps extending longitudinally from said open end of said outer bag.

3. The cold pack of claim 2 wherein said outer bag further comprises a fastener for securing said open end of said outer bag.

4. The cold pack of claim 3 wherein said outer bag is comprised of polypropylene material.

5. The cold pack of claim 4 wherein said inner bag is comprised of waterproof material.

6. The cold pack of claim 1 further comprising a pair of flexible members juxtaposed about said neck section of said inner bag to enable said neck section of said inner bag to be held in an open position upon application of pressure to said flexible members.

7. The cold pack of claim 6 wherein said neck section comprises
an outer layer defining a pair of spaced slits or apertures; and
a closure device for closing said open end of said inner bag disposed through said slits or apertures.

8. The cold pack of claim 1 wherein said attachments between said outer bag and said first and second attachment wings are selected from a group consisting of double stitching, sewing, gluing, heat sealing or ultrasonic welding.

9. The cold pack of claim 1 wherein said attachments between said outer bag and said first and second attachment wings are double stitch sewing.

10. A cold pack comprising:
a generally rectangularly shaped outer bag having a closed end, a first and a second opposing sides and an open end;
an inner bag located within said outer bag having a sealed closed end, a first and a second side seal defining opposing sides of said inner bag, and an open end; said open end of said inner bag having a neck section, wherein said neck section is narrower than said sealed closed end of said inner bag and wherein said neck section comprises an outer layer defining a pair of spaced slits or apertures;
first and second attachment wings each having an inside boundary and an outside boundary;
wherein each of said side seals has a first side and a second side, said first side of each side seal is directly attached to, or integrally formed with, only said inner bag, and at least a portion of said second side of each side seal is directly attached to, or integrally formed with, said inside boundary of one of said attachment wings;
wherein said first opposing side of said outer bag is directly attached to said first attachment wing at or along a first location other than said inside boundary of said first attachment wing, and said second opposing side of said outer bag is directly attached to said second attachment wing at or along a second location other than said inside boundary of said second attachment wing; wherein said attachments between said outer bag an said first and second attachment wings enable said inner bag to retain its shape relative to said outer bag; and
wherein said outer bag is separate from said neck section, in whole or in part, so that said outer bag may be folded or moved away from said neck section to expose said neck section, in whole or in part; and
a closure device for closing said open end of said inner bag, wherein said closure device is disposed through said spaced slits or apertures.

11. The cold pack of claim 10 wherein said closure device is completely covered by said outer bag.

12. The cold pack of claim 10 wherein said inner bag including said neck section and said closure device are disposed completely within said outer bag after ice or other cold substance has been received in said inner bag.

13. The cold pack of claim 12 further comprising a pair of flexible members juxtaposed about said neck section of said inner bag to enable said neck section of said inner bag to be held in an open position upon application of pressure to said flexible members.

14. The cold pack of claim 10 wherein said attachments between said outer bag and said first and second attachment wings are selected from a group consisting of double stitching, sewing, gluing, heat sealing or ultrasonic welding.

15. The cold pack of claim 10 wherein said attachments between said outer bag and said first and second attachment wings are double stitch sewing.

* * * * *

UNITED STATES PATENT AND TRADEMARK OFFICE
CERTIFICATE OF CORRECTION

PATENT NO.         : 7,972,368 B2
APPLICATION NO.    : 11/094046
DATED              : July 5, 2011
INVENTOR(S)        : Michael S. Boyd and Robert S. Woody It is certified that error appears in the above-identified patent and that said Letters Patent is hereby corrected as shown below:

In the Specification:

Column 4, line 14, delete "66" and insert therefore -- 36 --.

In the Claims:

Column 6, line 28, delete "an" and insert therefore -- and --.

Signed and Sealed this
Twenty-fifth Day of June, 2013

Teresa Stanek Rea
*Acting Director of the United States Patent and Trademark Office*